United States Patent [19]
Hino et al.

[11] Patent Number: 5,763,620
[45] Date of Patent: Jun. 9, 1998

[54] PROCESS FOR PRODUCING ALKYLENE SULFIDE

[76] Inventors: Youichi Hino, 1-80-1-506, Otori-nishi-machi, Sakai-shi, Osaka 593; Yoshitaka Arita; Norihiro Wakao, both of 4-52, Nakanoshima-cho, Suita-shi, Osaka 564; Ryuichi Ishikawa, 164-6, Kami, Sakai-shi, Osaka 593, all of Japan

[21] Appl. No.: 751,362

[22] Filed: Nov. 22, 1995

[30] Foreign Application Priority Data

Nov. 22, 1994 [JP] Japan .................. 6-2884115

[51] Int. Cl.$^6$ .................................................. C07D 331/02
[52] U.S. Cl. ........................................................... 549/1
[58] Field of Search ................................................ 549/1

[56] References Cited

U.S. PATENT DOCUMENTS

| | | | |
|---|---|---|---|
| 2,185,660 | 1/1940 | Coltof et al. | 549/1 |
| 3,417,099 | 12/1968 | Lautenschlaeger | 549/1 |
| 3,467,671 | 9/1969 | Sloar | 549/1 |
| 3,557,145 | 1/1971 | McFadden | 549/1 |
| 3,567,820 | 3/1971 | Searles et al. | 549/1 |
| 3,622,597 | 11/1971 | Fletcher | 549/1 |
| 3,687,976 | 8/1972 | Wright | 549/1 |
| 3,726,840 | 4/1973 | Gmilter et al. | 549/1 |
| 3,822,288 | 7/1974 | Labat | 549/1 |
| 5,304,656 | 4/1994 | Yano et al. | 549/1 |

FOREIGN PATENT DOCUMENTS 5-339257  12/1993  Japan .

*Primary Examiner*—Deborah C. Lambkin
*Attorney, Agent, or Firm*—Pendorf & Silverberg

[57] ABSTRACT

A process for producing an alkylene sulfide, which comprises the step of subjecting a mercaptoalkanol to an intramolecular dehydration reaction in the presence of an acidic dehydration catalyst, to produce the alkylene sulfide, in which the intramolecular dehydration reaction is conducted under at least one conditions of (1) to (3). (1) The intramolecular dehydration reaction is conducted in at least one solvent selected from the group consisting of compounds having an amide group N-substituted with a hydrocarbon group having from 1 to 6 carbon atoms, compounds having an unsubstituted amide group, compounds having a ureylene group N-substituted with a hydrocarbon group having from 1 to 6 carbon atoms, and compounds having an unsubstituted ureylene group. (2) The intramolecular dehydration reaction is conducted in a solvent under such temperature and pressure conditions that the reaction temperature T (°C.) and the boiling point tb (°C.) of the solvent at the reaction pressure satisfy equation $(tb-30) \leq T \leq tb$. (3) The intramolecular dehydration reaction is conducted in a solvent in the presence of a hydrocarbon having a boiling point at ordinary pressure of from 30° C. to 180° C. When the hydrocarbon has from 6 to 9 carbon atoms, the above-described effects are enhanced further. When the concentration of the hydrocarbon in the reaction mixture is maintained in the range of from 0.1 to 10% by weight, the above-described effects are enhanced even more.

21 Claims, No Drawings

PROCESS FOR PRODUCING ALKYLENE SULFIDE

FIELD OF THE INVENTION

The present invention relates to a process for producing an alkylene sulfide. More particularly, the present invention relates to a process for producing an alkylene sulfide from a mercaptoalkanol.

Because of their excellent reactivity, alkylene sulfides are useful in a wide range of fields as a raw material for medicines, agricultural chemicals and various industrial chemicals, a raw material for sulfurized polymers, etc.

BACKGROUND OF THE INVENTION

Known processes for producing an alkylene sulfide include a method in which mercaptoethanol is reacted in a liquid phase in the presence of a specific catalyst ($NaHSO_4$, $KHSO_4$) to synthesize ethylene sulfide, as disclosed in U.S. Pat. No. 3,467,671 and *J. Chem. Soc.* (C), pp. 1252–1256 (1969). Since this reaction tends to yield a large amount of polymers as by-products, these references disclose utilization of an inert gas or a hydrocarbon that vaporizes under the reaction conditions as a substance for accelerating the distillation of the yielded ethylene sulfide. However, even with such an expedient, inhibition of the side reactions producing polymers remains insufficient and the yield of ethylene sulfide is low. Thus, the above-described process is unsatisfactory for industrial production.

U.S. Pat. No. 3,622,597 discloses a process for synthesizing an alkylene sulfide by subjecting a mercaptoalkanol to a dehydration reaction in a specific solvent under specific reaction conditions with the aid of an acidic dehydration catalyst. This process is characterized in that in order to inhibit side polymerization reactions, specific reaction conditions are used and the yielded alkylene sulfide is taken out of the system without delay. Furthermore, U.S. Pat. No. 3,622,597 discloses optional use of an inert gas that does not react with alkylene sulfide, e.g., $CO_2$, $N_2$, Ar, $H_2O$, a lower alcohol, a lower alkane having 1 to 8 carbon atoms, or a volatile compound that does not react with alkylene sulfide, as a carrier gas. However, this process is also unsatisfactory for industrial production, because inhibition of the formation of by-product polymers is insufficient and the solvent denatures considerably to reduce reaction activity with the lapse of time.

SUMMARY OF THE INVENTION

An object of the present invention is to provide a process by which an alkylene sulfide can be stably produced in a highly selective manner from a mercaptoalkanol in a high yield over a prolonged period of time.

Other objects and effects of the present invention will be apparent from the following description.

The present invention relates to, as a first aspect, a process (hereinafter referred to simply as "the first process") for producing an alkylene sulfide represented by formula (1), the process comprising the step of subjecting a mercaptoalkanol represented by formula (2) to an intramolecular dehydration reaction in the presence of an acidic dehydration catalyst, to produce the alkylene sulfide represented by formula (1), the intramolecular dehydration reaction being conducted in at least one solvent selected from the group consisting of compounds having an amide group N-substituted with a hydrocarbon group having from 1 to 6 carbon atoms, compounds having an unsubstituted amide group, compounds having a ureylene group N-substituted with a hydrocarbon group having from 1 to 6 carbon atoms, and compounds having an unsubstituted ureylene group:

wherein $R^1$, $R^2$, $R^3$, and $R^4$ each may be the same or different and each independently represents a hydrogen atom, an alkyl group having from 1 to 4 carbon atoms, a phenyl group, a phenyl group substituted with an alkyl group having from 1 to 4 carbon atoms, or a benzyl group.

The present invention also relates to, as a second aspect, a process (hereinafter referred to simply as "the second process") for producing an alkylene sulfide represented by formula (1), the process comprising the step of subjecting a mercaptoalkanol represented by formula (2) to an intramolecular dehydration reaction in the presence of an acidic dehydration catalyst, to produce the alkylene sulfide represented by formula (1), the intramolecular dehydration reaction being conducted in a solvent under such temperature and pressure conditions that the reaction temperature T (°C.) and the boiling point tb (°C.) of the solvent at the reaction pressure satisfy equation (A):

$$(tb-30) \leq T \leq tb \tag{A}$$

The present invention further relates to, as a third aspect, a process (hereinafter referred to simply as "the third process") for producing an alkylene sulfide represented by formula (1), the process comprising the step of subjecting a mercaptoalkanol represented by formula (2) to an intramolecular dehydration reaction in the presence of an acidic dehydration catalyst, to produce the alkylene sulfide represented by formula (1), the intramolecular dehydration reaction being conducted in a solvent in the presence of a hydrocarbon having a boiling point at ordinary pressure of from 30° C. to 180° C.

In preferred embodiments of the present invention, the intramolecular dehydration reaction can be conducted under the condition which is a combination of at least two of the condition requirements of the first, second, and third processes. That is, the intramolecular dehydration reaction may be conducted:

(a) in the specific solvent of the first process and under the temperature and pressure conditions of the second process;

(b) in the specific solvent of the first process and in the presence of the hydrocarbon of the third process;

(c) in the specific solvent of the first process, under the temperature and pressure conditions of the second process, and in the presence of the hydrocarbon of the third process; or (d) under the temperature and pressure conditions of the second process and in the presence of the hydrocarbon of the third process.

DETAILED DESCRIPTION OF THE INVENTION

Examples of the mercaptoalkanols that can be used in the present invention include 2-mercaptoethanol, 1-mercapto-2- propanol, 2-mercapto-1-propanol, 1-mercapto-2-butanol, 3-mercapto-2-butanol, and 2-mercapto-1-phenylethanol.

Methods for feeding a mercaptoalkanol are not particularly limited. For example, a solvent and an acidic dehydration catalyst may be introduced into a reaction vessel before the mercaptoalkanol is fed thereto. Alternatively, a solvent alone may be introduced into a reaction vessel before the mercaptoalkanol and an acidic dehydration catalyst are fed thereto.

The acidic dehydration catalyst is not particularly limited, as long as it accelerates the intramolecular dehydration reaction of the mercaptoalkanol. Examples of the catalyst include sulfuric acid, phosphoric acid, the sulfuric ester of an alcohol having 1 to 20 carbon atoms, an alkanesulfonic acid, benzenesulfonic acid, and a benzenesulfonic acid in which the benzene ring has been substituted with an alkyl group (alkylbenzenesulfonic acid). Examples of the sulfuric ester of an alcohol include methyl sulfate, ethyl sulfate, butyl sulfate, and dodecyl sulfate. Examples of the alkanesulfonic acid include methanesulfonic acid and dodecanesulfonic acid. Examples of the benzenesulfonic acid in which the benzene ring has been substituted with an alkyl group include toluenesulfonic acid and ethylbenzenesulfonic acid. Especially preferred of these are sulfuric acid and the sulfo-containing acidic dehydration catalysts including methanesulfonic acid because of their high reactivity with sulfuric acid being particularly preferred. Also usable as the catalyst include a compound that is converted into any of the above-enumerated acidic dehydration catalysts during the reaction.

Methods for introducing an acidic dehydration catalyst are not particularly limited. The catalyst may be introduced into a reaction vessel beforehand, or may be fed together with a feedstock.

The amount of the acidic dehydration catalyst to be used varies depending on the reaction temperature, the amount of the mercaptoalkanol fed, etc. The amount of the acidic dehydration catalyst is preferably from 0.1 to 50% by weight, more preferably from 0.5 to 40% by weight, based on the amount of the solvent. Catalyst amounts smaller than 0.1% by weight tend to result in a reduced reaction rate and reduced production efficiency. Catalyst amounts larger than 50% by weight tend to result in side reactions including polymerization of the starting compound or yielded reaction product and in denaturation of the solvent.

Although the solvent is not particularly limited as long as it is a solvent for use in producing a mercaptoalkanol, it is preferably one which is inert to both the mercaptoalkanol and the alkylene sulfide to be yielded.

For use in the first process according to the present invention, such a solvent is selected from compounds having an amide group N-substituted with a hydrocarbon group having 1 to 6 carbon atoms, compounds having an unsubstituted amide group, compounds having a ureylene group N-substituted with a hydrocarbon group having 1 to 6 carbon atoms, and compounds having an unsubstituted ureylene group. Specific examples of the solvent used in the first process include linear amide compounds such as dimethylformamide, diethylformamide, and dimethylacetamide; cyclic amide compounds such as N-alkylpyrrolidones including N-methylpyrrolidone and N-ethylpyrrolidone; and urea compounds such as tetramethylurea, 1,3-dimethyl-2-imidazolidinone, and 1,3-diethyl-2-imidazolidinone. Among these, N-alkylpyrrolidones, 1,3-dimethyl-2-imidazolidinone, and 1,3-diethyl-2-imidazolidinone, which all are cyclic compounds, are preferred since they can be easily separated from the reaction products, alkylene sulfide and water, due to the large difference in boiling point between such solvents and the alkylene sulfide or water, and that they are highly stable and undergo little denaturation. Use of N-methylpyrrolidone is especially preferred because it is highly effective in inhibiting side reactions. A mixture of two or more of these solvents may also be used.

In the second and third processes, the solvent is also preferably selected from compounds having an amide group N-substituted with a hydrocarbon group having 1 to 6 carbon atoms, compounds having an unsubstituted amide group, compounds having a ureylene group N-substituted with a hydrocarbon group having 1 to 6 carbon atoms, and compounds having an unsubstituted ureylene group, examples of which are as given above.

In addition to these solvents, polyalkylene glycols and ether compounds may also be used in the second and third processes. Preferred examples of the ether compounds for use as the solvent include monoalkyl ethers of polyalkylene glycols and dialkyl ethers of polyalkylene glycols, because these ethers are less denatured. Examples of the polyalkylene glycols include diethylene glycol, dipropylene glycol, and triethylene glycol. Examples of the polyalkylene glycol monoalkyl ethers include diethylene glycol monomethyl ether, diethylene glycol monobutyl ether, dipropylene glycol monomethyl ether, and triethylene glycol monomethyl ether. Examples of the polyalkylene glycol dialkyl ethers include diethylene glycol diethyl ether and triethylene glycol dimethyl ether. A mixture of two or more of these may be used.

In the second and third processes according to the present invention, an alkanol having 2 to 12 carbon atoms such as, e.g., 2-ethylhexanol, decanol, ethylene glycol, or propylene glycol may also be used as a solvent.

In the second process according to the present invention, the reaction temperature T (°C.) of the dehydration reaction satisfies equation (A) with respect to the boiling point tb (°C.) of the solvent at the reaction pressure:

$$(tb-30) \leq T \leq tb \tag{A}$$

The boiling point tb (°C.) and the reaction temperature T (°C.) in the second process preferably satisfy equation (B):

$$(tb-15) \leq T \leq tb \tag{B}$$

and more preferably satisfy equation (C):

$$(tb-8) \leq T \leq tb \tag{C}$$

If the boiling point tb (°C.) and the reaction temperature T (°C.) do not satisfy equation (A) given above, there are cases where the yielded alkylene sulfide undergoes polymerization or other reactions to result in a reduced yield and in an insufficient conversion of the mercaptoalkanol used as the starting compound.

The reaction temperature T (°C.) in the dehydration step of the first to third processes of the present invention is preferably regulated to the range of from 80° to 200° C., more preferably from 100° to 160° C. Reaction temperatures lower than 80° C. tend to result in a reduced reaction rate and reduced production efficiency. Reaction temperatures higher than 200° C. tend to result in side reactions, e.g., polymerization of the starting compound or yielded reaction product, and in denaturation of the solvent.

The regulation of reaction temperature may be accomplished, for example, by passing water or steam through a coil or jacket attached to the reaction vessel, while monitoring the temperature of the reaction system. Methods for temperature regulation are not limited thereto, and any other methods capable of temperature regulation may be used.

The reaction pressure in the dehydration reaction varies depending on the solvent and starting compound used, reaction temperature, and other reaction conditions. It is however, preferred to regulate the reaction pressure in the range of from 5 to 500 mmHg, more preferably from 10 to 400 mmHg, particularly preferably from 50 to 300 mmHg. Reaction pressures lower than the lower limit tend to necessitate an expensive apparatus for carrying out the reaction at such a low pressure and an apparatus for cooling and collecting the yielded alkylene sulfide, water, etc. In such a case, if these apparatus are omitted in carrying out the reaction, the proportion of the alkylene sulfide which flies out and remains uncollected becomes large, so that not only a reduced yield results but also the process is uneconomical. If the reaction pressure exceeds the upper limit, it tends to be difficult to take the yielded alkylene sulfide out of the reaction system by distillation, so that the alkylene sulfide undergoes side reactions, resulting in a reduced yield.

The regulation of reaction pressure may be accomplished, for example, by operating a vacuum pump through a pressure regulator ganged therewith, while monitoring the pressure within the reaction system. However, methods for pressure regulation are not limited thereto, and any other methods capable of pressure regulation may be used.

In the third process according to the present invention, the specific hydrocarbon is caused to be present in the reaction system for the purposes of inhibiting denaturation of the solvent, enhancing the stability of the yielded alkylene sulfide to enable efficient collection thereof, etc.

The hydrocarbon used in the third process has a boiling point at ordinary pressure of from 30° to 180° C., preferably from 60° to 170° C. If a hydrocarbon having a boiling point lower than 30° C. is caused to be present in the reaction system, there are cases where the hydrocarbon cannot be efficiently condensed and collected because it is highly volatile, resulting in a considerable hydrocarbon loss. If a hydrocarbon having a boiling point higher than 180° C. is used, there are cases where the effect of the coexistence of the hydrocarbon with the solvent and the catalyst becomes insufficient.

Hydrocarbons having from 6 to 9 carbon atoms are preferably used in the third process because these hydrocarbons not only are highly effective when coexist with the catalyst and the solvent but also tend to be efficiently condensed and collected. Examples of such hydrocarbons include aromatic hydrocarbons such as benzene, toluene, xylene, pseudocumene, ethylbenzene, and mesitylene; halogenated aromatic hydrocarbons such as fluorobenzene, and chlorobenzene; and aliphatic hydrocarbons such as hexane, heptane, octane, cyclohexane, and methylcyclohexane. These may be used as a mixture of two or more thereof.

When a hydrocarbon is caused to be present in the reaction mixture in the present invention, the concentration of the hydrocarbon in the reaction mixture is preferably regulated. The concentration of the hydrocarbon in the reaction mixture is preferably kept in the range of from 0.1 to 10% by weight, more preferably from 0.5 to 6% by weight.

If the hydrocarbon concentration in the reaction mixture is lower than 0.1% by weight, the coexistence of the hydrocarbon with the solvent and the catalyst tends to be less effective in, e.g., improving the yield of an alkylene sulfide. If the hydrocarbon concentration in the reaction mixture exceeds 10% by weight, a reduced alkylene sulfide yield tends to result. Although the reasons why the presence of the hydrocarbon in a solvent produces such unexpected effects have not been elucidated, it is presumed that the hydrocarbon functions to regulate the solvent so as to have liquid properties suitable for the reaction and serves to inhibit denaturation of the yielded alkylene sulfide.

The hydrocarbon concentration in the reaction mixture can be regulated by, for example, a method in which feeding of a hydrocarbon is initiated simultaneously with initiation of the reaction and, after a given concentration is reached, this concentration is maintained. Alternatively, a method may be used in which a hydrocarbon is introduced to a given concentration prior to initiation of the reaction and this concentration is maintained throughout the reaction.

In the present invention, the dehydration reaction can be conducted under the condition which is a combination of at least two of the condition requirements of the first, second, and third processes of the present invention for enhancing the effect of the present invention.

In carrying out the processes of the present invention, either a semi-batch process or a continuous process may be employed.

One embodiment of the semi-batch process for carrying out the process of the present invention is described below, but the present invention is not construed as being limited thereto.

A solvent and a catalyst are introduced into a reaction tank equipped with a distilling column. To this reaction tank is fed a feedstock composed of a mercaptoalkanol and a hydrocarbon (which ingredients may be fed either after being mixed with each other or through separate lines). Reaction is then conducted in a liquid phase, while the reaction temperature and the reaction pressure are kept at respective given values. A replenishment of the solvent may be added beforehand to the feedstock in an amount corresponding to the solvent amount to be lost by distillation. The alkylene sulfide yielded is continuously collected from the top of the distilling column together with water and the hydrocarbon. If side reactions take place to form polymers, the polymers accumulate in the reaction tank. It is therefore preferred in this case to stop the feeding of the feedstock after the lapse of a certain time period and discharge the residual reaction mixture from the reaction tank. Thereafter, a fresh solvent and a fresh catalyst are introduced into the reaction tank to repeat the reaction. In another embodiment, a solvent, a catalyst, and a hydrocarbon are introduced into a reaction tank, and a mercaptoalkanol is fed as a feedstock. The alkylene sulfide yielded is collected together with water, and the reaction can be repeated. The residual reaction mixture may be reused after undesired substances, e.g., polymers, are removed therefrom.

One embodiment of the continuous process for carrying out the processes of the present invention is described below, but the present invention is not construed as being limited thereto.

A solvent and a catalyst are introduced into a reaction tank equipped with a distilling column. To this reaction tank is then continuously fed a feedstock composed of a mercaptoalkanol, a solvent, a hydrocarbon, and a catalyst, and reaction is conducted in a liquid phase, while the reaction temperature and the reaction pressure are kept at respective given values. The alkylene sulfide yielded is continuously collected from the top of the distilling column together with water and the hydrocarbon, while the liquid present in the reaction tank is partly discharged continuously or intermittently in an amount corresponding to the increased liquid amount due to feeding and reaction. The liquid discharged from the reaction tank may be reused after undesired substances, e.g., polymers, are removed therefrom.

Alkylene sulfides are highly reactive and readily undergo polymerization. A stabilizer for alkylene sulfides may be used in the present invention for the purpose of inhibiting such polymerization (side reaction). Examples of the stabilizer include divalent sulfur compounds described in U.S. Pat. No. 2,185,660, e.g., hydrogen sulfide, alkyl mercaptans, alkyl sulfides, and carbon disulfide, and thioacetamide described in U.S. Pat. No. 3,557,145. The stabilizer may be introduced into the reaction vessel either beforehand or together with the mercaptoalkanol.

A carrier gas may be passed through the reaction system for the purpose of rapidly taking the yielded alkylene sulfide out of the reaction system. However, if a non-condensable carrier gas is used, the alkylene sulfide and other substances fly out during the collection of the alkylene sulfide in an amount corresponding to the vapor pressure. It is therefore preferred to avoid unnecessary use of a non-condensable carrier gas. Examples of usable carrier gases include gases inert to the reaction of the present invention, such as $CO_2$, $N_2$, Ar, He, and lower alkanes having 1 to 4 carbon atoms.

According to the processes of the present invention for alkylene sulfide production, an alkylene sulfide can be stably produced in a highly selective manner from a mercaptoalkanol in high yield over a prolonged period of time. The processes of the present invention are therefore suitable for the industrial production of alkylene sulfides from mercaptoalkanols.

In particular, in the third process, the coexistence of a hydrocarbon with the solvent and the catalyst is exceedingly effective in the reaction of mercaptoethanol for producing ethylene sulfide. This process is hence especially suitable for the production of ethylene sulfide.

The present invention will be explained below in more detail by reference to Examples and Comparative Examples, but the present invention should not be construed as being limited thereto in any way.

The conversion of a mercaptoalkanol and the yield of an alkylene sulfide are defined by the following equations:

Conversion of mercaptoalkanol (%) =

$$\frac{\text{molar amount of consumed mercaptoalkanol}}{\text{molar amount of supplied mercaptoalkanol}} \times 100$$

Yield of alkylene sulfide (%) =

$$\frac{\text{molar amount of yielded alkylene sulfide}}{\text{molar amount of supplied mercaptoalkanol}} \times 100$$

In the Examples and Comparative Examples given below, a 500-cc flask equipped with a distillation part comprising an electromagnetic reflux valve, a condenser, and a column was used as a reaction vessel. In the flask, the feedstock feed opening and the distillation part each was fitted with a thermometer. The reaction part was also fitted with a thermometer. Reaction temperature was regulated with an oil bath, while reaction pressure was regulated with a pressure regulator connected to a vacuum pump.

EXAMPLE 1-1

Into a reaction vessel were introduced 150 g of 1,3-dimethyl-2-imidazolidinone as a solvent and 60 g of methanesulfonic acid as a catalyst. After the reaction temperature and the reaction pressure were regulated to 100° C. and 75 mmHg, respectively, 1-mercapto-2-propanol was fed as a feedstock at a rate of 40 g/hr. Simultaneously with initiation of the reaction, propylene sulfide and water began to distill out through the top of the reaction vessel. The distillation rate was regulated with the electromagnetic reflux valve so as not to exceed the feed rate, while the temperatures of the respective parts of the reaction vessel were maintained. The reaction was thus continued for 30 hours, throughout which the liquid distilled out through the top of the vessel was collected. The collected liquid separated into an organic phase and an aqueous phase. The distillate obtained at 4 hours after initiation of the reaction and that obtained at the time of completion of the reaction (30 hours after the initiation) were analyzed by gas chromatography to determine the conversion of the 1-mercapto-2-propanol and the yield of propylene sulfide.

EXAMPLE 1-2

Reaction and analysis were carried out in the same manner as in Example 1-1, except that 150 g of N-methylpyrrolidone was used as a solvent, 2 g of sulfuric acid was used as a catalyst, and 1-meracpto-2-propanol was fed as a feedstock at a rate of 35 g/hr.

Experimental conditions used in Examples 1-1 and 1-2 and the results obtained are shown in Table 1.

TABLE 1

| Example | Feedstock | Feed rate (g/hr) | Pre-introduced solvent and catalyst | Weight (g) | Reaction conditions | | | Conversion of mercapto-alkanol (%) | Yield of alkylene sulfide (%) | Boiling point of solvent** (°C.) |
|---|---|---|---|---|---|---|---|---|---|---|
| | | | | | Temperature (°C.) | Pressure (mmHg) | Time (hr) | | | |
| 1-1 | 1-mercapto-2-propanol (total) | 40.0 | 1,3-dimethyl-2-imidazolidinone | 150 | 100 | 75 | 4 | 100 | 87 | 145 |
| | | 40.0 | methanesulfonic acid | 60 | | | 30 | 100 | 87 | |
| 1-2 | 1-mercapto-2-propanol (total) | 35.0 | N-methyl-pyrrolidone | 150 | 140 | 400 | 4 | 100 | 86 | 179 |
| | | 35.0 | $H_2SO_4$ | 2 | | | 20 | 99 | 85 | |

**Boiling point of solvent at the reaction pressure

EXAMPLE 2-1

Into a reaction vessel were introduced 150 g of 1,3-dimethyl-2-imidazolidinone as a solvent and 20 g of sulfuric acid as a catalyst. After the reaction temperature and the reaction pressure were regulated to 150° C. and 300 mmHg, respectively, a 33 wt % toluene solution of 2-mercaptoethanol was fed as a feedstock at a rate of 60 g/hr. Simultaneously with initiation of the reaction, ethylene sulfide, water, and toluene began to distill out through the top of the reaction vessel. The distillation rate was regulated with the electromagnetic reflux valve so as not to exceed the feed rate, while the temperatures of the respective parts of the reaction vessel were maintained. The reaction was thus continued for 30 hours, throughout which the liquid distilled out through the top of the vessel was collected. The collected liquid separated into an organic phase and an aqueous phase. The distillate obtained at 4 hours after initiation of the reaction, the distillate obtained at the time of completion of the reaction (30 hours after the initiation), and a part of the final bottom group were analyzed by gas chromatography to determine the conversion of the 2-mercaptoethanol and the yield of ethylene sulfide.

Experimental conditions used in Example 2-1 and the results obtained therein are shown in Table 2.

COMPARATIVE EXAMPLE 2

An experiment was carried out without using any solvent. Into a reaction vessel were introduced 150 g of 1-mercapto-2-propanol as a starting compound and 2 g of sulfuric acid. After the reaction temperature and the reaction pressure were regulated to 140° C. and 300 mmHg, respectively, 1-mercapto-2-propanol was fed as a feedstock at a rate of 35 g/hr. Simultaneously with initiation of the reaction, propylene sulfide and water began to distill out through the top of the reaction vessel. The reaction was stopped at 3 hours after initiation thereof because the viscosity of the bottom liquid in the flask increased at that time. The distillate was analyzed by gas chromatography to determine the conversion of the 1-mercapto-2-propanol and the yield of propylene sulfide.

COMPARATIVE EXAMPLE 3

An experiment was carried out in which a hydrocarbon was not caused to be present in the reaction mixture. Into a reaction vessel were introduced 150 g of triethylene glycol dimethyl ether as a solvent and 7 g of sulfuric acid as a catalyst, and 2-mercaptoethanol was fed as a feed stock at a rate of 10 g/hr. The boiling point of the solvent at the reaction pressure was 151° C.

It was found that when a hydrocarbon was not caused to be present in the reaction mixture, white solid matters were

TABLE 2

| Example | Feedstock | Feed rate (g/hr) | Pre-introduced solvent and catalyst | Weight (g) | Reaction conditions Temperature (°C.) | Reaction conditions Pressure (mmHg) | Time (hr) | Conversion of mercapto-alkanol (%) | Yield of alkylene sulfide (%) | Concentration of hydrocarbon* (wt %) | Boiling point of solvent** (°C.) |
|---|---|---|---|---|---|---|---|---|---|---|---|
| 2-1 | 2-mercaptoethanol | 20.0 | 1,3-dimethyl-2-imidazolidinone | 150 | 150 | 300 | 4 | 100 | 90 | 6.9 | 189 |
|  | toluene | 40.0 | H₂SO₄ | 20 |  |  | 30 | 100 | 90 | 7.0 |  |
|  | (total) | 60.0 |  |  |  |  |  |  |  |  |  |

*Concentration of hydrocarbon in the reaction mixture
**Boiling point of solvent at the reaction pressure

COMPARATIVE EXAMPLE 1

Reaction and analysis were carried out in the same manner as in Example 1, except that 150 g of triethylene glycol monobutyl ether, which is the poly(alkylene oxide) monoalkyl ether used in an Example of U.S. Pat. No. 3,622,597, was used. (The boiling point of the solvent at the reaction pressure used was 204° C.)

deposited in the distillation column equipped at the top of the reaction vessel. Thus, there was a problem of clogging and it was difficult to produce an ethylene sulfide in an industrial scale.

Experimental conditions used in Comparative Examples 1 to 3 and the results obtained therein are shown in Table 3.

TABLE 3

| Comparative Example | Feedstock | Feed rate (g/hr) | Pre-introduced solvent and catalyst | Weight (g) | Reaction conditions Temperature (°C.) | Reaction conditions Pressure (mmHg) | Time (hr) | Conversion of mercapto-alkanol (%) | Yield of alkylene sulfide (%) | Boiling point of solvent** (°C.) |
|---|---|---|---|---|---|---|---|---|---|---|
| 1 | 1-mercapto-2-propanol | 35.0 | triethylene glycol monobutyl ether | 150 | 140 | 100 | 4 | 99 | 76 | 204 |
|  | (total) | 35.0 | H₂SO₄ | 2 |  |  | 20 | 95 | 61 |  |
| 2 | 1-mercapto-2-propanol | 35.0 | 1-mercapto-2-propanol | 150 | 140 | 300 | 3 | 91 | 39 | 142 |
|  | (total) | 35.0 | H₂SO₄ | 2 |  |  |  |  |  |  |

TABLE 3-continued

| Compara-tive Example | Feedstock | Feed rate (g/hr) | Pre-introduced solvent and catalyst | Weight (g) | Reaction conditions Temp-erature (°C.) | Pres-sure (mmHg) | Time (hr) | Conver-sion of mercapto-alkanol (%) | Yield of alkylene sulfide (%) | Boiling point of solvent** (°C.) |
|---|---|---|---|---|---|---|---|---|---|---|
| 3 | 2-mercapto-ethanol | 10.0 | triethylene glycol dimethyl ether | 150 | 110 | 100 | 4 | 97 | 79 | 151 |
|  | (total) | 10.0 | H₂SO₄ | 2 |  |  | 20 | 92 | 59 |  |

**Boiling point of solvent at the reaction pressure

EXAMPLE 3-1

Into a reaction vessel were introduced 150 g of N-methylpyrrolidone as a solvent and 2 g of sulfuric acid as a catalyst. The mixing of N-methylpyrrolidone with sulfuric acid resulted in considerable heat generation. After the reaction temperature and the reaction pressure were regulated to 140° C. and 150 mmHg, respectively, 1-mercapto-2-propanol was fed as a feedstock at a rate of 35 g/hr. Simultaneously with initiation of the reaction, propylene sulfide and water began to distill out through the top of the reaction vessel. The distillation rate was regulated with the electromagnetic reflux valve so as not to exceed the feed rate, while the temperatures of the respective parts of the reaction vessel were maintained. The reaction was thus continued for 20 hours, throughout which the liquid distilled out through the top of the vessel was collected. The collected liquid separated into an organic phase and an aqueous phase. The distillate obtained at 4 hours after initiation of the reaction and that obtained at the time of completion of the reaction (20 hours after the initiation) were analyzed by gas chromatography to determine the conversion of the 1-mercapto-2-propanol and the yield of propylene sulfide.

EXAMPLE 3-2

Reaction and analysis were carried out in the same manner as in Example 3-1, except that 20 g of sulfuric acid was used as a catalyst and 1-mercapto-2-propanol was fed as a feedstock at a rate of 30 g/hr.

EXAMPLE 3-3

Reaction and analysis were carried out in the same manner as in Example 3-1, except that 150 g of 1,3-dimethyl-2-imidazolidinone as a solvent and 2.5 g of sulfuric acid as a catalyst were used, and that 2-mercapto-1-phenylethanol was fed as a feedstock at a rate of 20 g/hr.

EXAMPLE 3-4

Reaction and analysis were carried out in the same manner as in Example 3-1, except that the reaction temperature was regulated to a temperature higher than the boiling point of the solvent at the reaction pressure.

Experimental conditions used in Examples 3-1 to 3-4 and the results obtained therein are shown in Table 4.

TABLE 4

| Example | Feedstock | Feed rate (g/hr) | Pre-introduced solvent and catalyst | Weight (g) | Reaction conditions Temp-erature (°C.) | Pres-sure (mmHg) | Time (hr) | Conver-sion of mercapto-alkanol (%) | Yield of alkylene sulfide (%) | Boiling point of solvent** (°C.) |
|---|---|---|---|---|---|---|---|---|---|---|
| 3-1 | 1-mercapto-2-propanol | 35.0 | N-methyl-pyrrolidone | 150 | 140 | 150 | 4 | 100 | 95 | 147 |
|  | (total) | 35.0 | H₂SO₄ | 2 |  |  | 20 | 100 | 94 |  |
| 3-2 | 1-mercapto-2-propanol | 30.0 | N-methyl-pyrrolidone | 150 | 110 | 50 | 4 | 100 | 92 | 117 |
|  | (total) | 30.0 | H₂SO₄ | 20 |  |  | 48 | 100 | 91 |  |
| 3-3 | 2-mercapto-1-phenyl-ethanol | 20.0 | 1,3-dimethyl-2-imidazolidinone | 150 | 105 | 20 | 4 | 100 | 91 | 111 |
|  | (total) | 20.0 | H₂SO₄ | 2.5 |  |  | 48 | 100 | 90 |  |
| 3-4 | 1-mercapto-2-propanol | 35.0 | N-methyl-pyrrolidone | 150 | 148 | 150 | 4 | 80 | 76 | 147 |
|  | (total) | 35.0 | H₂SO₄ | 2 |  |  | 20 | 85 | 80 |  |

**Boiling point of solvent at the reaction pressure

EXAMPLE 4-1

Into a reaction vessel were introduced 150 g of N-methylpyrrolidone as a solvent and 0.3 g of sulfuric acid as a catalyst. After the reaction temperature and the reaction pressure were regulated to 150° C. and 300 mmHg, respectively, a 33 wt % xylene solution of 2-mercaptoethanol was fed as a feedstock at a rate of 90 g/hr. Simultaneously with initiation of the reaction, ethylene sulfide and water began to distill out through the top of the reaction vessel. The distillation rate was regulated with the electromagnetic reflux valve so as not to exceed the feed rate, while the temperatures of the respective parts of the reaction vessel were maintained. The reaction was thus continued for 20 hours, throughout which the liquid distilled out through the top of the vessel was collected. The collected liquid separated into an organic phase and an aqueous phase. The distillate obtained at 4 hours after initiation of the reaction and that obtained at the time of completion of the reaction (20 hours after the initiation) were analyzed by gas chromatography to determine the conversion of the 2-mercaptoethanol and the yield of ethylene sulfide.

EXAMPLE 4-2

Reaction and analysis were carried out in the same manner as in Example 4-1, except that 7.5 g of sulfuric acid was used as a catalyst.

EXAMPLE 4-3

Reaction and analysis were carried out in the same manner as in Example 4-1, except that 12 g of sulfuric acid was used as a catalyst and a 50 wt % xylene solution of 1-mercapto-2-propanol was fed as a feedstock at a rate of 80 g/hr.

EXAMPLE 4-4

Reaction and analysis were carried out in the same manner as in Example 4-1, except that 60 g of p-toluenesulfonic acid was used as a catalyst and a 50 wt % mesitylene solution of 1-mercapto-2-propanol was fed as a feedstock at a rate of 80 g/h.

EXAMPLE 4-5

Reaction and analysis were carried out in the same manner as in Example 4-1, except that 150 g of 1,3-dimethyl-2-imidazolidinone as a solvent and 0.9 g of sulfuric acid as a catalyst were used, and that a 33 wt % hexane solution of 2-mercapto-1-phenylethanol was fed as a feedstock at a rate of 30 g/h.

EXAMPLE 4-6

Reaction and analysis were carried out in the same manner as in Example 4-1, except that 150 g of N,N-dimethylacetamide as a solvent and 30 g of sulfuric acid as a catalyst were used, and that a 40 wt % cyclohexane solution of 2-mercaptoethanol was fed as a feedstock at a rate of 50 g/hr.

EXAMPLE 4-7

Reaction and analysis were carried out in the same manner as in Example 4-1, except that the reaction temperature was regulated to a temperature lower by at least 30° C. than the boiling point of the solvent at the reaction pressure, that 150 g of 1,3-dimethyl-2-imidazolidinone as a solvent and 12 g of sulfuric acid as a catalyst were used, and that a 50 wt % toluene solution of 1-mercapto-2-propanol was fed as a feedstock at a rate of 60 g/hr.

EXAMPLE 4-8

Reaction and analysis were carried out in the same manner as in Example 4-1, except that 150 g of N,N-dimethylformamide as a solvent and 25 g of sulfuric acid as a catalyst were used, and that a 50 wt % toluene solution of 2-mercaptoethanol was fed as a feedstock at a rate of 20 g/hr.

EXAMPLE 4-9

Reaction and analysis were carried out in the same manner as in Example 4-1, except that 2 g of sulfuric acid was used as a catalyst and a 60 wt % toluene solution of 1-mercapto-2-propanol was fed as a feedstock at a rate of 50 g/hr.

EXAMPLE 4-10

Reaction and analysis were carried out in the same manner as in Example 4-1, except that 150 g of N-ethylpyrrolidone as a solvent and 30 g of p-toluenesulfonic acid as a catalyst were used, and that a 50 wt % xylene solution of 2-mercaptoethanol was fed as a feedstock at a rate of 40 g/hr.

Experimental conditions used in Examples 4-1 to 4-10 and the results obtained therein are shown in Table 5.

TABLE 5

| Example | Feedstock | Feed rate (g/hr) | Pre-introduced solvent and catalyst | Weight (g) | Reaction conditions Temperature (°C.) | Pressure (mmHg) | Time (hr) | Conversion of mercapto-alkanol (%) | Yield of alkylene sulfide (%) | Concentration of hydrocarbon* (wt %) | Boiling point of solvent** (°C.) |
|---|---|---|---|---|---|---|---|---|---|---|---|
| 4-1 | 2-mercapto-ethanol | 30.0 | N-methyl pyrrolidone | 150 | 150 | 300 | 4 | 100 | 91 | 9.6 | 169 |
|  | xylene (total) | 60.0 90.0 | H₂SO₄ | 0.3 |  |  | 20 | 100 | 90 | 9.8 |  |
| 4-2 | 2-mercapto-ethanol | 30.0 | N-methyl pyrrolidone | 150 | 140 | 150 | 4 | 100 | 96 | 3.2 | 147 |
|  | xylene (total) | 60.0 90.0 | H₂SO₄ | 7.5 |  |  | 20 | 100 | 95 | 3.2 |  |
| 4-3 | 1-mercapto-2-propanol | 40.0 | N-methyl pyrrolidone | 150 | 135 | 130 | 4 | 100 | 97 | 5.1 | 143 |
|  | xylene (total) | 40.0 80.0 | H₂SO₄ | 12 |  |  | 30 | 100 | 95 | 5.2 |  |
| 4-4 | 1-mercapto-2-propanol | 40.0 | N-methyl pyrrolidone | 150 | 130 | 100 | 4 | 100 | 86 | 3.9 | 141 |
|  | mesitylene (total) | 40.0 80.0 | p-toluene-sulfonic acid | 60 |  |  | 20 | 100 | 85 | 4.1 |  |

TABLE 5-continued

| Example | Feedstock | Feed rate (g/hr) | Pre-introduced solvent and catalyst | Weight (g) | Reaction conditions | | Time (hr) | Conversion of mercapto-alkanol (%) | Yield of alkylene sulfide (%) | Concentration of hydrocarbon* (wt %) | Boiling point of solvent** (°C.) |
|---|---|---|---|---|---|---|---|---|---|---|---|
| | | | | | Temperature (°C.) | Pressure (mmHg) | | | | | |
| 4-5 | 2-mercapto-1-phenyl ethanol | 10.0 | 1,3-dimethyl-2-imidazolidinone | 150 | 160 | 200 | 4 | 100 | 92 | 0.8 | 175 |
| | hexane (total) | 20.0 30.0 | $H_2SO_4$ | 0.9 | | | 40 | 100 | 91 | 0.9 | |
| 4-6 | 2-mercapto-ethanol | 20.0 | N,N-dimethyl acetamide | 150 | 100 | 220 | 4 | 100 | 86 | 9.4 | 128 |
| | cyclohexane (total) | 30.0 50.0 | $H_2SO_4$ | 30 | | | 20 | 100 | 85 | 9.6 | |
| 4-7 | 1-mercapto-2-propanol | 30.0 | 1,3-dimethyl-2-imidazolidinone | 150 | 110 | 150 | 4 | 100 | 81 | 17.1 | 175 |
| | toluene (total) | 30.0 60.0 | $H_2SO_4$ | 12 | | | 20 | 100 | 79 | 17.5 | |
| 4-8 | 2-mercapto-ethanol | 10.0 | N,N-dimethyl formamide | 150 | 80 | 150 | 4 | 99 | 90 | 35.4 | 101 |
| | toluene (total) | 10.0 20.0 | $H_2SO_4$ | 25 | | | 48 | 98 | 89 | 36.5 | |
| 4-9 | 1-mercapto-2-propanol | 30.0 | 1,3-dimethyl-2-imidazolidine | 150 | 130 | 50 | 4 | 100 | 93 | 2.5 | 134 |
| | toluene (total) | 20.0 50.0 | $H_2SO_4$ | 2 | | | 20 | 100 | 92 | 2.8 | |
| 4-10 | 2-mercapto-ethanol | 20.0 | N-ethyl-pyrrolidone | 150 | 140 | 100 | 4 | 100 | 85 | 9.0 | 155 |
| | xylene (total) | 20.0 40.0 | p-toluene-sulfonic acid | 30 | | | 30 | 100 | 83 | 9.1 | |

*Concentration of hydrocarbon in the reaction mixture
**Boiling point of solvent at the reaction pressure

EXAMPLE 5-1

Into a reaction vessel were introduced 150 g of diethylene glycol monobutyl ether as a solvent and 20 g of sulfuric acid as a catalyst. After the reaction temperature and the reaction pressure were regulated to 110° C. and 30 mmHg, respectively, a 25 wt % octane solution of 2-mercaptoethanol was fed as a feedstock at a rate of 40 g/hr. Simultaneously with initiation of the reaction, ethylene sulfide and water began to distill out through the top of the reaction vessel. The distillation rate was regulated with the electromagnetic reflux valve so as not to exceed the feed rate, while the temperatures of the respective parts of the reaction vessel were maintained. The reaction was thus continued for 20 hours, throughout which the liquid distilled out through the top of the vessel was collected. The collected liquid separated into an organic phase and an aqueous phase. The distillate obtained at 4 hours after initiation of the reaction and that obtained at the time of completion of the reaction (20 hours after the initiation) were analyzed by gas chromatography to determine the conversion of the 2-mercaptoethanol and the yield of ethylene sulfide.

EXAMPLE 5-2

Reaction and analysis were carried out in the same manner as in Example 5-1, except that 150 g of triethylene glycol dimethyl ether as a solvent and 15 g of sulfuric acid as a catalyst were used, and that a 33 wt % toluene solution of 1-mercapto-2-propanol was fed as a feedstock at a rate of 30 g/hr.

EXAMPLE 5-3

Reaction and analysis were carried out in the same manner as in Example 5-1, except that the reaction temperature was regulated to a temperature lower by at least 30° C. than the boiling point of the solvent at the reaction pressure, that 150 g of diethylene glycol monobutyl ether as a solvent and 4 g of sulfuric acid as a catalyst were used, and that a 50 wt % mesitylene solution of 1-mercapto-2-propanol was fed as a feedstock at a rate of 60 g/hr.

Experimental conditions used in Examples 5-1 to 5-3 and the results obtained therein are shown in Table 6.

TABLE 6

| Example | Feedstock | Feed rate (g/hr) | Pre-introduced solvent and catalyst | Weight (g) | Reaction conditions | | Time (hr) | Conversion of mercapto-alkanol (%) | Yield of alkylene sulfide (%) | Concentration of hydrocarbon* (wt %) | Boiling point of solvent** (°C.) |
|---|---|---|---|---|---|---|---|---|---|---|---|
| | | | | | Temperature (°C.) | Pressure (mmHg) | | | | | |
| 5-1 | 2-mercapto-ethanol | 10.0 | diethylene glycol monobutyl ether | 150 | 110 | 30 | 4 | 100 | 84 | 2.6 | 132 |
| | octane (total) | 30.0 40.0 | $H_2SO_4$ | 20 | | | 20 | 100 | 83 | 2.8 | |

TABLE 6-continued

| Example | Feedstock | Feed rate (g/hr) | Pre-introduced solvent and catalyst | Weight (g) | Reaction conditions Temperature (°C.) | Pressure (mmHg) | Time (hr) | Conversion of mercapto-alkanol (%) | Yield of alkylene sulfide (%) | Concentration of hydrocarbon* (wt %) | Boiling point of solvent** (°C.) |
|---|---|---|---|---|---|---|---|---|---|---|---|
| 5-2 | 1-mercapto-2-propanol | 10.0 | triethylene glycol dimethyl ether | 150 | 120 | 50 | 4 | 100 | 85 | 1.0 | 132 |
|  | toluene | 20.0 | H$_2$SO$_4$ | 15 |  |  | 20 | 100 | 83 | 1.1 |  |
|  | (total) | 30.0 |  |  |  |  |  |  |  |  |  |
| 5-3 | 1-mercapto-2-propanol | 30.0 | diethylene glycol monobutyl ether | 150 | 130 | 100 | 4 | 100 | 80 | 15.1 | 164 |
|  | mesitylene | 30.0 | H$_2$SO$_4$ | 4 |  |  | 20 | 95 | 65 | 15.5 |  |
|  | (total) | 60.0 |  |  |  |  |  |  |  |  |  |

*Concentration of hydrocarbon in the reaction mixture
**Boiling point of solvent at the reaction pressure The results given above show that the processes of the present invention are capable of efficiently and stably yielding alkylene sulfides in high yield over a prolonged time period.

According to the processes of the present invention for alkylene sulfide production, an alkylene sulfide can be stably produced in a highly selective manner from a mercaptoalkanol in high yield over a prolonged period of time.

By using a suitable combination of the following features (1) to (3) of the present invention, it is possible to stably produce an alkylene sulfide in a more highly selective manner in higher yield over long.

(1) The intramolecular dehydration reaction is conducted in at least one solvent selected from the group consisting of compounds having an amide group N-substituted with a hydrocarbon group having from 1 to 6 carbon atoms, compounds having an unsubstituted amide group, compounds having a ureylene group N-substituted with a hydrocarbon group having from 1 to 6 carbon atoms, and compounds having an unsubstituted ureylene group.

(2) The intramolecular dehydration reaction is conducted in a solvent under such temperature and pressure conditions that the reaction temperature T (°C.) and the boiling point tb (°C.) of the solvent at the reaction pressure satisfy equation (A):

$$(tb-30) \leq T \leq tb \qquad (A)$$

(3) The intramolecular dehydration reaction is conducted in a solvent in the presence of a hydrocarbon having a boiling point at ordinary pressure of from 30° C. to 180° C. When the hydrocarbon has from 6 to 9 carbon atoms, the above-described effects are enhanced further. When the concentration of the hydrocarbon in the reaction mixture is maintained in the range of from 0.1 to 10% by weight, the above-described effects are enhanced even more.

While the invention has been described in detail and with reference to specific embodiments thereof, it will be apparent to one skilled in the art that various changes and modifications can be made therein without departing from the spirit and scope thereof.

What is claimed is:

1. A process for producing an alkylene sulfide represented by formula (1), said process comprising the step of subjecting a mercaptoalkanol represented by formula (2) to an intramolecular dehydration reaction in the presence of an acidic dehydration catalyst, to produce said alkylene sulfide represented by formula (1), said intramolecular dehydration reaction being conducted in at least one solvent selected from the group consisting of compounds having an amide group N-substituted with a hydrocarbon group having from 1 to 6 carbon atoms, compounds having an unsubstituted amide group, compounds having a ureylene group N-substituted with a hydrocarbon group having from 1 to 6 carbon atoms, and compounds having an unsubstituted ureylene group:

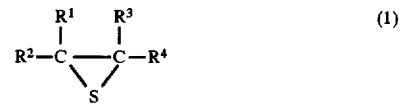

(1)

(2)

wherein $R^1$, $R^2$, $R^3$, and $R^4$ may be the same or different and each independently represents a hydrogen atom, an alkyl group having from 1 to 4 carbon atoms, a phenyl group, a phenyl group substituted with an alkyl group having from 1 to 4 carbon atoms, or a benzyl group.

2. A process for producing an alkylene sulfide as claimed in claim 1, wherein said intramolecular dehydration reaction being conducted in a solvent under such temperature and pressure conditions that the reaction temperature T (°C.) and the boiling point tb (°C.) of said solvent at the reaction pressure satisfy equation (A):

$$(tb-30) \leq T \leq tb \qquad (A).$$

3. A process for producing an alkylene sulfide as claimed in claim 1, wherein said intramolecular dehydration reaction being conducted in a solvent in the presence of a hydrocarbon having a boiling point at ordinary pressure of from 30° C. to 180° C.

4. A process for producing an alkylene sulfide as claimed in claim 3, wherein said hydrocarbon has from 6 to 9 carbon atoms.

5. A process for producing an alkylene sulfide as claimed in claim 4, wherein in said intramolecular dehydration reaction, the concentration of said hydrocarbon in a reaction mixture is from 0.1 to 10% by weight.

6. A process for producing an alkylene sulfide as claimed in claim 1, wherein said intramolecular dehydration reaction being conducted in a solvent in the presence of a hydrocarbon having a boiling point at ordinary pressure of from 30° C. to 180° C.

7. A process for producing an alkylene sulfide as claimed in claim 6, wherein said hydrocarbon has from 6 to 9 carbon atoms.

8. A process for producing an alkylene sulfide as claimed in claim 6, wherein, in said intramolecular dehydration reaction, the concentration of said hydrocarbon in a reaction mixture is from 0.1 to 10% by weight.

9. A process for producing an alkylene sulfide as claimed in claim 1, wherein said acidic dehydration catalyst is a compound selected from the group consisting of sulfuric acid, phosphoric acid, an alkyl sulfate having an alkyl group having from 1 to 20 carbon atoms, an alkanesulfonic acid, benzenesulfonic acid, and an alkylbenzenesulfonic acid.

10. A process for producing an alkylene sulfide as claimed in claim 1, wherein said intramolecular dehydration reaction is conducted at a temperature of from 80° to 200° C. and at a pressure of from 5 to 500 mmHg.

11. A process for producing an alkylene sulfide represented by formula (1), said process comprising the step of subjecting a mercaptoalkanol represented by formula (2) to an intramolecular dehydration reaction in the presence of an acidic dehydration catalyst, to produce said alkylene sulfide represented by formula (1), said intramolecular dehydration reaction being conducted in a solvent under such temperature and pressure conditions that the reaction temperature T (°C.) and the boiling point tb (°C.) of said solvent at the reaction pressure satisfy equation (A):

$$(tb - 30) \leq T \leq tb \qquad (A)$$

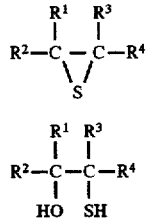

(1)

(2)

wherein $R^1$, $R^2$, $R^3$, and $R^4$ may be the same or different and each independently represents a hydrogen atom, an alkyl group having from 1 to 4 carbon atoms, a phenyl group, a phenyl group substituted with an alkyl group having from 1 to 4 carbon atoms, or a benzyl group.

12. A process for producing an alkylene sulfide as claimed in claim 11, wherein said intramolecular dehydration reaction being conducted in the presence of a hydrocarbon having a boiling point at ordinary pressure of from 30° C. to 180° C.

13. A process for producing an alkylene sulfide as claimed in claim 12, wherein said hydrocarbon has from 6 to 9 carbon atoms.

14. A process for producing an alkylene sulfide as claimed in claim 12, wherein, in said intramolecular dehydration reaction, the concentration of said hydrocarbon in a reaction mixture is from 0.1 to 10% by weight.

15. A process for producing an alkylene sulfide as claimed in claim 11, wherein said acidic dehydration catalyst is a compound selected from the group consisting of sulfuric acid, phosphoric acid, an alkyl sulfate having an alkyl group having from 1 to 20 carbon atoms, an alkanesulfonic acid, benzenesulfonic acid, and an alkylbenzenesulfonic acid.

16. A process for producing an alkylene sulfide as claimed in claim 11, wherein said intramolecular dehydration reaction is conducted at a temperature of from 80° to 200° C. and at a pressure of from 5 to 500 mmHg.

17. A process for producing an alkylene sulfide represented by formula (1), said process comprising the step of subjecting a mercaptoalkanol represented by formula (2) to an intramolecular dehydration reaction in the presence of an acidic dehydration catalyst, to produce said alkylene sulfide represented by formula (1), said intramolecular dehydration reaction being conducted in a solvent in the presence of a hydrocarbon having a boiling point at ordinary pressure of from 30° C. to 180° C.:

wherein $R^1$, $R^2$, $R^3$, and $R^4$ may be the same or different and each independently represents a hydrogen atom, an alkyl group having from 1 to 4 carbon atoms, a phenyl group, a phenyl group substituted with an alkyl group having from 1 to 4 carbon atoms, or a benzyl group.

18. A process for producing an alkylene sulfide as claimed in claim 17, wherein said hydrocarbon has from 6 to 9 carbon atoms.

19. A process for producing an alkylene sulfide as claimed in claim 17, wherein in said intramolecular dehydration reaction, the concentration of said hydrocarbon in a reaction mixture is from 0.1 to 10% by weight.

20. A process for producing an alkylene sulfide as claimed in claim 17, wherein said acidic dehydration catalyst is a compound selected from the group consisting of sulfuric acid, phosphoric acid, an alkyl sulfate having an alkyl group having from 1 to 20 carbon atoms, an alkanesulfonic acid, benzenesulfonic acid, and an alkylbenzenesulfonic acid.

21. A process for producing an alkylene sulfide as claimed in claim 17, wherein said intramolecular dehydration reaction is conducted at a temperature of from 80° to 200° C. and at a pressure of from 5 to 500 mmHg.

* * * * *

UNITED STATES PATENT AND TRADEMARK OFFICE
CERTIFICATE OF CORRECTION

PATENT NO.   : 5,763,620
DATED        : June 9, 1998
INVENTOR(S)  : Youichi Hino et al.

It is certified that error appears in the above-identified patent and that said Letters Patent is hereby corrected as shown below: On the title page, item

[30]         Foreign Application Priority Data

Nov. 22, 1994  [JP]   Japan .........................................6-288415

Signed and Sealed this

Twenty-ninth Day of December, 1998

*Attest:*

BRUCE LEHMAN

*Attesting Officer*           Commissioner of Patents and Trademarks